(12) United States Patent
Baker et al.

(10) Patent No.: US 7,811,310 B2
(45) Date of Patent: Oct. 12, 2010

(54) MULTISTAGE SPINAL FIXATION LOCKING MECHANISM

(75) Inventors: Daniel R. Baker, Seattle, WA (US); Carly A. Thaler, Seattle, WA (US); Alex E. Kunzler, Issaquah, WA (US); Anthony V. Finazzo, Lake Forest Park, WA (US)

(73) Assignee: Spinefrontier, Inc, Beverly, MA (US)

( * ) Notice: Subject to any disclaimer, the term of this patent is extended or adjusted under 35 U.S.C. 154(b) by 678 days.

(21) Appl. No.: 11/121,414

(22) Filed: May 4, 2005

(65) Prior Publication Data

US 2006/0264933 A1    Nov. 23, 2006

(51) Int. Cl.
*A61B 17/70* (2006.01)
(52) U.S. Cl. .................. 606/267; 606/268; 606/305
(58) Field of Classification Search .............. 606/61, 606/264–279, 300–321, 246
See application file for complete search history.

(56) References Cited

U.S. PATENT DOCUMENTS

| | | | |
|---|---|---|---|
| 4,611,581 A | 9/1986 | Steffee |
| 4,805,602 A | 2/1989 | Puno et al. |
| 4,854,311 A | 8/1989 | Steffee |
| 4,887,596 A | 12/1989 | Sherman |
| 4,946,458 A | 8/1990 | Harms et al. |
| 5,113,685 A | 5/1992 | Asher et al. |
| 5,129,900 A | 7/1992 | Asher et al. |
| 5,207,678 A | 5/1993 | Harms et al. |
| 5,261,303 A | 11/1993 | Strippgen |
| 5,312,404 A | 5/1994 | Asher et al. |
| 5,360,431 A | 11/1994 | Puno et al. |
| 5,443,467 A | 8/1995 | Biedermann et al. |
| 5,466,237 A | 11/1995 | Byrd, III et al. |
| 5,474,555 A | 12/1995 | Puno et al. |
| 5,476,463 A | 12/1995 | Boachie-Adjei et al. |
| 5,522,816 A | 6/1996 | Dinello et al. |
| 5,534,001 A | 7/1996 | Schlapfer et al. |
| 5,549,608 A | 8/1996 | Errico et al. |
| 5,554,157 A | 9/1996 | Errico et al. |
| 5,569,247 A | 10/1996 | Morrison |
| 5,575,792 A | 11/1996 | Errico et al. |
| 5,578,033 A | 11/1996 | Errico et al. |
| 5,584,834 A | 12/1996 | Errico et al. |
| 5,586,984 A | 12/1996 | Errico et al. |
| 5,609,593 A | 3/1997 | Errico et al. |
| 5,609,594 A | 3/1997 | Errico et al. |
| 5,643,263 A | 7/1997 | Simonson |

(Continued)

*Primary Examiner*—Eduardo C Robert
*Assistant Examiner*—Christina Negrelli
(74) *Attorney, Agent, or Firm*—AKC Patents LLC; Aliki K. Collins (57) ABSTRACT

The present invention relates to a locking mechanism and method of locking the relative positions of a fixation device like a bone screw and of a stabilization device like a rod. The locking mechanism includes a seat, a washer and a cap. The seat includes a bottom portion configured to receive the fixation device such that a socket of the bottom portion engages part of the fixation device and prevents the fixation device from passing entirely therethrough. The seat further includes a side portion configured to receive the stabilization device, a washer and a cap. When the washer and cap are fully engaged with the seat, the fixation device may be locked independent of the stabilization device. The locking mechanism may also include a locking element for locking the stabilization device.

30 Claims, 7 Drawing Sheets

U.S. PATENT DOCUMENTS

| | | | |
|---|---|---|---|
| 5,643,265 A | 7/1997 | Errico et al. | |
| 5,647,873 A | 7/1997 | Errico et al. | |
| 5,672,176 A | 9/1997 | Biedermann et al. | |
| 5,683,392 A | 11/1997 | Richelsoph et al. | |
| 5,688,274 A | 11/1997 | Errico et al. | |
| 5,690,630 A | 11/1997 | Errico et al. | |
| 5,713,898 A | 2/1998 | Stücker et al. | |
| 5,725,527 A | 3/1998 | Biedermann et al. | |
| 5,725,528 A | 3/1998 | Errico et al. | |
| 5,725,588 A | 3/1998 | Errico et al. | |
| 5,728,098 A | 3/1998 | Sherman et al. | |
| 5,733,285 A | 3/1998 | Errico et al. | |
| 5,733,286 A | 3/1998 | Errico et al. | |
| 5,738,685 A | 4/1998 | Halm et al. | |
| 5,741,255 A | 4/1998 | Krag et al. | |
| 5,743,907 A | 4/1998 | Asher et al. | |
| 5,776,135 A | 7/1998 | Errico et al. | |
| 5,782,833 A | 7/1998 | Haider | |
| 5,797,911 A | 8/1998 | Sherman et al. | |
| 5,817,094 A | 10/1998 | Errico et al. | |
| 5,863,293 A | 1/1999 | Richelsoph | |
| 5,879,350 A | 3/1999 | Sherman et al. | |
| 5,882,350 A | 3/1999 | Ralph et al. | |
| 5,885,285 A | 3/1999 | Simonson | |
| 5,885,286 A | 3/1999 | Sherman et al. | |
| 5,891,145 A | 4/1999 | Morrison et al. | |
| 5,954,725 A | 9/1999 | Sherman et al. | |
| 5,964,760 A | 10/1999 | Richelsoph | |
| 5,989,250 A | 11/1999 | Wagner et al. | |
| 6,010,503 A | 1/2000 | Richelsoph et al. | |
| 6,019,759 A | 2/2000 | Rogozinski | |
| 6,022,350 A | 2/2000 | Genem | |
| 6,053,917 A | 4/2000 | Sherman et al. | |
| 6,063,089 A | 5/2000 | Errico et al. | |
| 6,074,391 A | 6/2000 | Metz-Stavenhagen et al. | |
| 6,077,262 A * | 6/2000 | Schlapfer et al. | 606/305 |
| 6,090,111 A | 7/2000 | Nichols | |
| 6,132,430 A | 10/2000 | Wagner | |
| 6,132,434 A | 10/2000 | Sherman et al. | |
| 6,224,598 B1 | 5/2001 | Jackson | |
| 6,248,105 B1 | 6/2001 | Schläpfer et al. | |
| 6,280,442 B1 | 8/2001 | Barker et al. | |
| 6,287,311 B1 | 9/2001 | Sherman et al. | |
| 6,290,703 B1 | 9/2001 | Ganem | |
| 6,355,038 B1 | 3/2002 | Pisharodi | |
| 6,361,535 B2 | 3/2002 | Jackson | |
| 6,368,321 B1 | 4/2002 | Jackson | |
| 6,371,957 B1 | 4/2002 | Amrein et al. | |
| 6,416,515 B1 | 7/2002 | Wagner | |
| 6,440,132 B1 | 8/2002 | Jackson | |
| 6,451,021 B1 | 9/2002 | Ralph et al. | |
| 6,454,773 B1 | 9/2002 | Sherman et al. | |
| 6,458,132 B2 | 10/2002 | Choi | |
| 6,471,705 B1 | 10/2002 | Biedermann et al. | |
| 6,485,491 B1 | 11/2002 | Farris et al. | |
| 6,485,492 B1 | 11/2002 | Halm et al. | |
| 6,520,963 B1 | 2/2003 | McKinley | |
| 6,524,315 B1 | 2/2003 | Selvitelli et al. | |
| 6,540,749 B2 | 4/2003 | Schäfer et al. | |
| 6,547,790 B2 | 4/2003 | Harkey, III et al. | |
| 6,554,834 B1 | 4/2003 | Crozet et al. | |
| 6,562,040 B1 | 5/2003 | Wagner | |
| 6,565,565 B1 * | 5/2003 | Yuan et al. | 606/272 |
| 6,595,992 B1 | 7/2003 | Wagner et al. | |
| 6,613,050 B1 | 9/2003 | Wagner et al. | |
| 6,641,586 B2 | 11/2003 | Varieur | |
| 6,660,004 B2 | 12/2003 | Barker et al. | |
| 6,733,502 B2 | 5/2004 | Altarac et al. | |
| 6,755,829 B1 * | 6/2004 | Bono et al. | 606/61 |
| 6,786,903 B2 * | 9/2004 | Lin | 606/23 |
| 6,793,657 B2 * | 9/2004 | Lee et al. | 606/61 |
| 6,896,677 B1 * | 5/2005 | Lin | 606/266 |
| 2002/0120272 A1 | 8/2002 | Yuan et al. | |
| 2003/0125742 A1 | 7/2003 | Yuan et al. | |

* cited by examiner

MULTISTAGE SPINAL FIXATION LOCKING MECHANISM

FIELD OF THE INVENTION

The present invention relates generally to prostheses for treating spinal pathologies, and more specifically to a bone interface anchor for holding a stabilization rod.

BACKGROUND OF THE INVENTION

Various methods of spinal immobilization have been used in the treatment of spinal instability and displacement. The most common treatment for spinal stabilization is immobilization of the joint by surgical fusion, or arthrodesis. This has been known for almost a century. In many cases, however, pseudoarthrosis is a problem, particularly in cases involving fusion across the lumbosacral articulation and when more than two vertebrae are fused together. Early in the century, post operative external immobilization such as the use of splints and casts was the favored method of spinal fixation. As surgical techniques became more sophisticated, various methods of internal and external fixation were developed.

Internal fixation refers to therapeutic methods of stabilization that are wholly internal to the patient and include commonly known devices such as bone plates, screws, rods and pins. External fixation, in contrast, involves at least some portion of the stabilization device being located external to the patient's body. As surgical technologies and procedures became more advanced and the likelihood of infection decreased, internal fixation became the favored method of immobilization since it is less restrictive on the patient.

Internal fixation of the spine may be used to treat a variety of disorders including kyphosis, spondylolisthesis and rotation, segmental instability, such as disc degeneration and/or fracture caused by disease, trauma, congenital defects and tumor diseases.

One of the main challenges associated with spinal fixation is securing the fixation device to the spine without damaging the spinal cord. The pedicles of a vertebra are commonly used for fixation as they generally offer an area that is strong enough to hold the fixation device in place to fix the treatment area even when the patient suffers from degenerative instability such as osteoporosis. Early fixation devices involved the use of screws extending through the facets and into the pedicles.

Current fixation devices and hardware systems used internally for spinal fixation in modern surgical procedures are generally designed to meet one or more criteria, such as: providing rigidity as is indicated, generally along the long axis of the patient's spine; accommodating a broad variation in the size and shape of the spinal member with which it is used; having the capability of handling the stresses and strains to which the devices will be subjected resulting from movement of the spine; and providing easy surgical access during both implantation and removal of the implant.

Of these factors, the most difficult to achieve may very well be providing easy surgical access when the implant is being deployed and/or removed by surgeon. In particular, surgeons often wish to fit, test, adjust and refit fixation devices numerous times during a procedure in order to ensure that the device is optimally positioned. This is particularly important when dealing with the spinal column due to the risk of paralysis.

One example of a device designed as an attempt to meet the above-described criteria is disclosed in U.S. Pat. No. 5,466, 237. The fixation device disclosed includes what is described as a variable position locking anchor having a bone screw and a seat.

The disclosed device uses a nut as a locking mechanism. As disclosed, the nut is tightened to the seat to compress an attached rod along a longitudinal axis of the screw, causing the screw to engage in mating contact with the seat and thereby locking the screw in place. In use, it is difficult to maintain proper positioning of the fixation device while tightening a nut or other such locking mechanism.

It would be preferable, however, if the screw could be locked independently of the rod. It would also be preferable if the screw could be locked without compressing the rod and the screw. It would further be preferable if the locking mechanism included a partial or preliminary lock for assisting the surgeon in fitting the implant prior to finally locking the implant in place.

The present invention includes a novel fixation device that overcomes the disadvantages of the prior art.

BRIEF SUMMARY OF THE INVENTION

According to an aspect of the present invention, there is provided a locking mechanism configured to engage and lock a relative position of a bone fixation device and a relative position of a stabilization device. The locking mechanism comprises: a seat having a bottom portion configured to receive the fixation device and prevent the fixation device from passing entirely therethrough and a side portion configured to receive the stabilization device; a washer configured to engage the side portion of the seat between the stabilization device and the fixation device; and a cap configured to engage the washer and the side portion of the seat to lock the fixation device with respect to the bottom portion of the seat independent of the stabilization device.

According to another aspect of the present invention, there is provided a locking mechanism configured to engage and lock a relative position of a bone fixation device and a relative position of a stabilization device. The locking mechanism comprises: a seat having a bottom portion configured to receive the fixation device and prevent the fixation device from passing entirely therethrough and a side portion configured to receive the stabilization device; a washer with wings configured to engage channels of the side portion of the seat between the stabilization device and the fixation device, the wings have receivers configured for alignment with a locking channel of the side portion of the seat; and a cap configured to engage the receivers of the wings of the washer and the locking channel of the seat to lock the fixation device with respect to the bottom portion of the seat independent of the stabilization device; and a locking element configured for locking the stabilization with respect to the seat by causing compression of the stabilization device and the washer.

According to another aspect of the present invention, there is provided a method for locking the relative positions of a fixation device and a stabilization device comprising: placing a fixation device through a bottom portion of a seat; engaging a washer having a receiver with a side portion of the seat having a locking channel such that the receiver of the washer and the locking channel of the seat are aligned; placing a stabilization device in a side portion of the seat; and placing a cap with a male member atop the seat such that the male member engages the locking channel and the receiver; and locking the fixation device with respect to the seat.

DETAILED DESCRIPTION OF THE INVENTION

Turning initially to FIGS. 1A-C and 2A-D, FIGS. 1A-C show exploded perspective views of the locking mechanism of the present invention, and FIGS. 2A-D show cross sectional views of the locking mechanism of the present invention. The locking mechanism 100 is configured to engage and lock the relative position of a fixation device 104 with respect to the seat 102. The locking mechanism may also be configured to lock the relative position of the stabilization device 106 with respect to the seat 102. Preferably, the fixation device 104 can be locked independent of the stabilization device 106.

The locking mechanism 100 includes a seat 102, a washer 108 and a cap 110. The seat 102 includes a bottom portion 114 that is configured to receive the fixation device 104 such that a socket 116 of the bottom portion 114 engages part of the fixation device 104 and prevents the fixation device 104 from passing entirely therethrough.

Figure 5A:
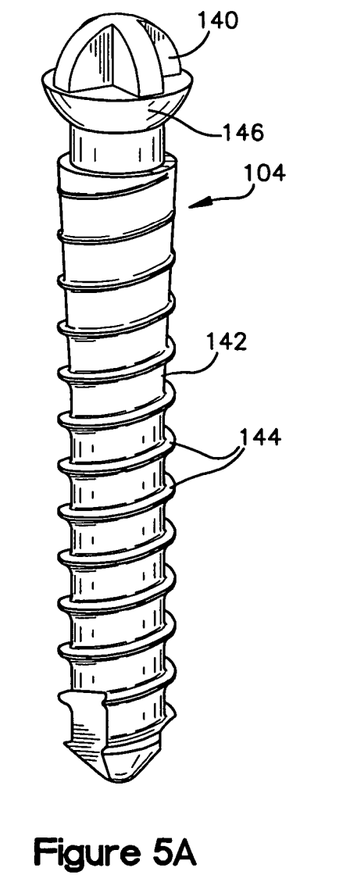
FIGS. 5A-B are perspective views of exemplary fixation devices with which the present invention can be used.
Figure 5B:
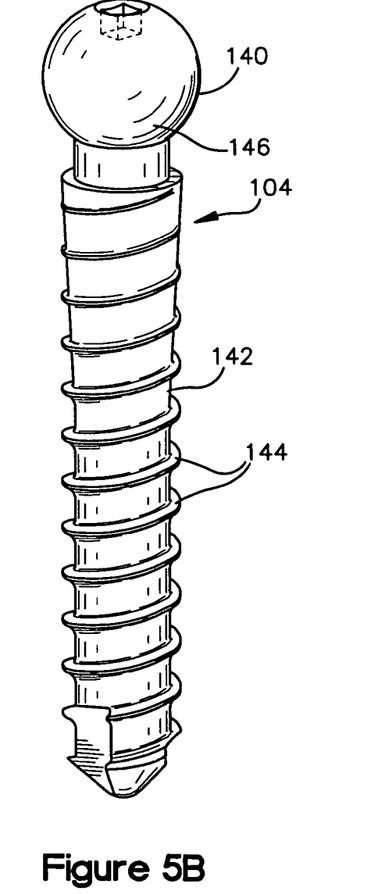

The fixation device 104 may be, for example, a screw having a head 140 and a shaft 142 with threads 144. Examples of fixation devices 104 are shown in FIGS. 5A and 5B. In order to prevent the fixation device 104 from passing entirely through the seat 102, the seat 102 preferably includes a hole 118 that is larger than the shaft 142 and smaller than the head 140. When the fixation device 104 is forced toward the bottom portion 114 of the seat 102, the socket 116 of the bottom portion 114 of the seat 102 engages the head 140 of the fixation device 104. In addition, the socket 116 of the bottom portion 114 may be tapered to receive and engage the fixation device 104.

The seat 102 also includes a side portion 112 that is configured to receive the stabilization device 106, the washer 108 and the cap 110. The stabilization device 106 may be, for example, a rod, and the side portion 112 of the seat 102 may include a channel 124 for receiving the stabilization device 106.

The washer 108 and side portion 112 are configured for engagement between the fixation device 104 and stabilization device 106. The washer 108 and side portion 112 may be, for example, slidably engageable, rotatably engageable and/or snapably engageable. In the presently preferred embodiment, the washer 108 and side portion 112 are rotatably engageable. To facilitate engagement with the washer 108, the side portion 112 of the seat 102 may include at least one groove 120 configured to accept the washer 108. The washer 108 is at least partially engageable with the side portion 112 such that the fixation device 104 is caused to become at least partially locked so as to facilitate placement and alignment of the stabilization device 106.

Once partially engaged, the washer 108 is preferably disengageable from the side portion 112 so as to facilitate a change in placement or alignment of the fixation device 104. The washer 108 may also be configured such that the washer 108 permits access to the fixation device 104 when the washer 108 is at least partially engaged with the side portion 112.

The washer 108 and the cap 110 are also configured for engagement, as are the cap 110 and the side portion 112. For example, the side portion 112 may be configured to receive both the washer 108 and the cap 110 such that the washer 108 and the cap 110 cooperate in mating engagement. The side portion 112 may be further configured such that the mated washer 108 and cap 110 are lockingly engageable with the side portion 112 to cause locking of the fixation device 104 independent of the stabilization device 106.

The locking mechanism 100 may also include a locking element 201 for locking the position of the stabilization device 106. Examples of the locking element (per claim 8) include a screw, a breakaway screw, a washer, a 90 degree washer, a linear wedge, a washer and nut and a snap-in lock. The stabilization device 106 may also be locked independent of the fixation device 104.

Figure 1A:
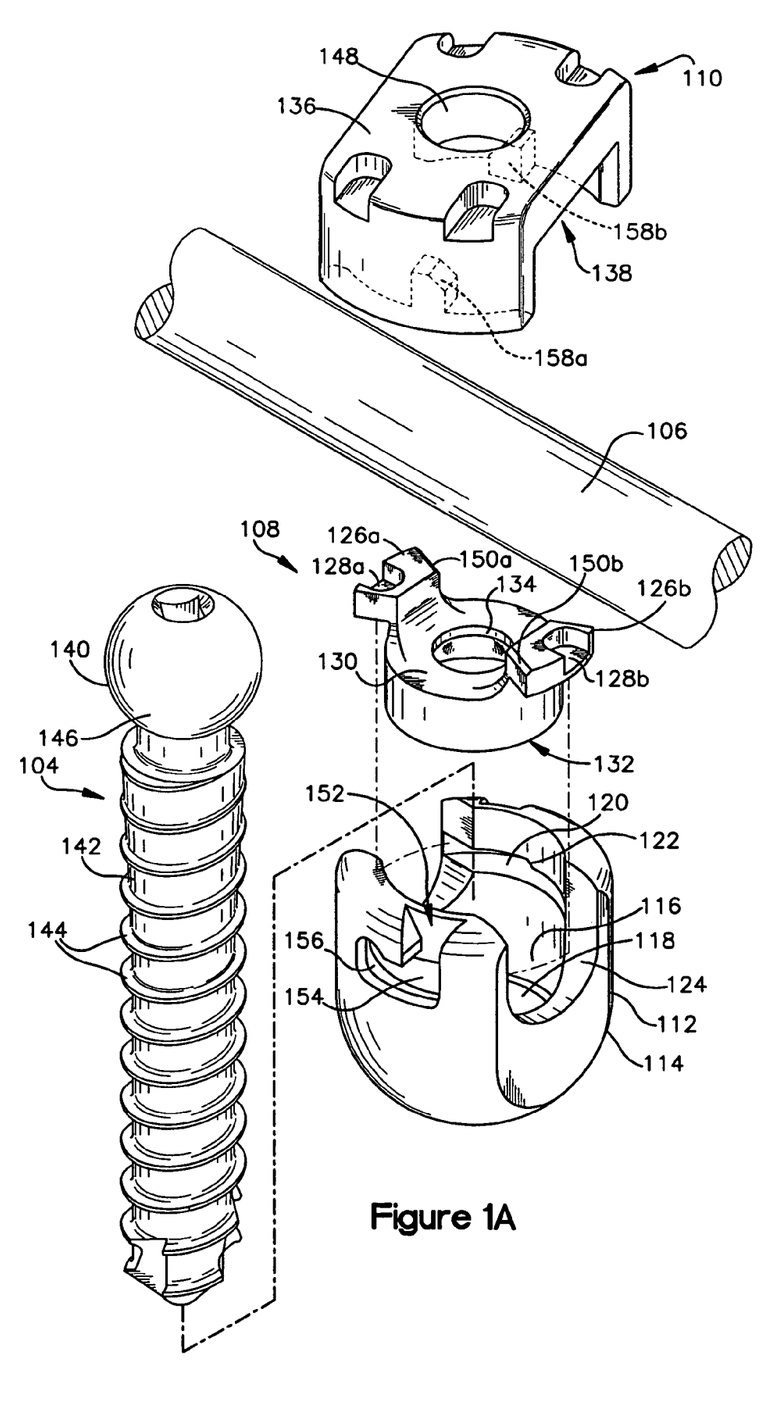
FIGS. 1A-C are exploded perspective views of the locking mechanism of the present invention with a fixation device and a stabilization device.
Figure 1B:
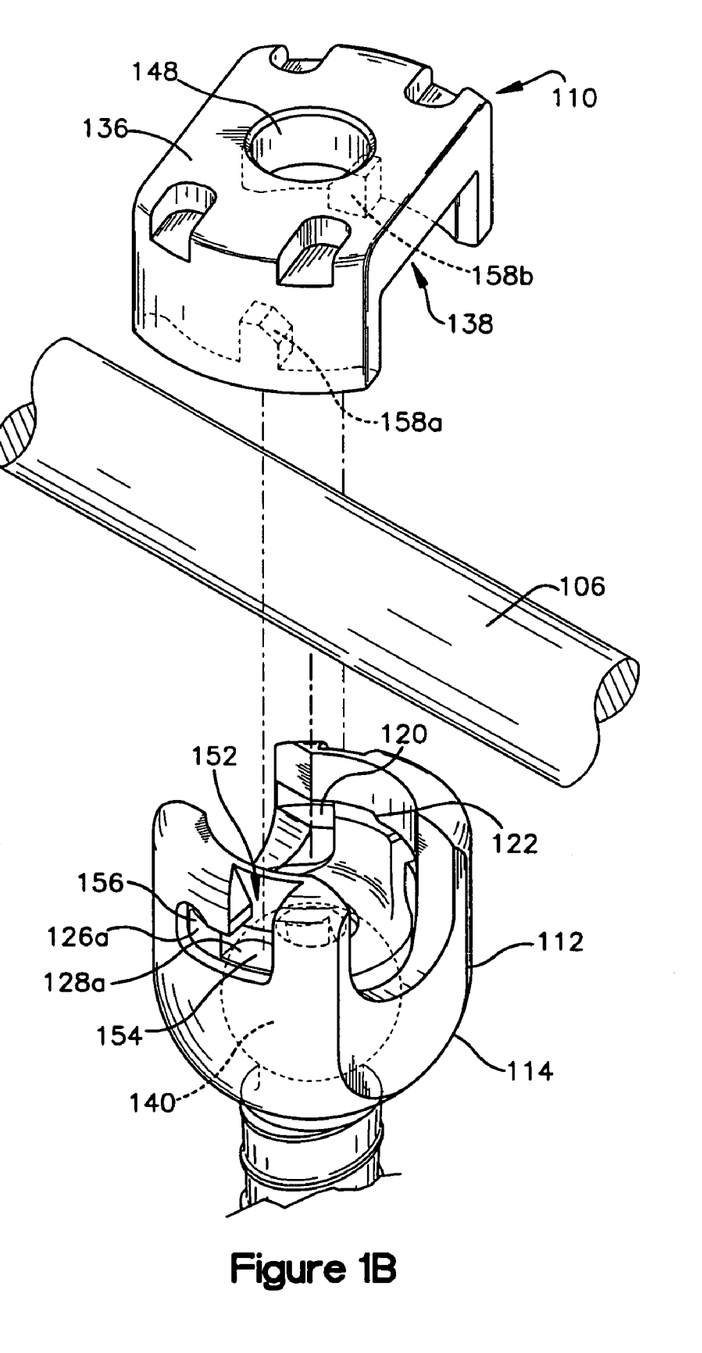
Figure 1C:
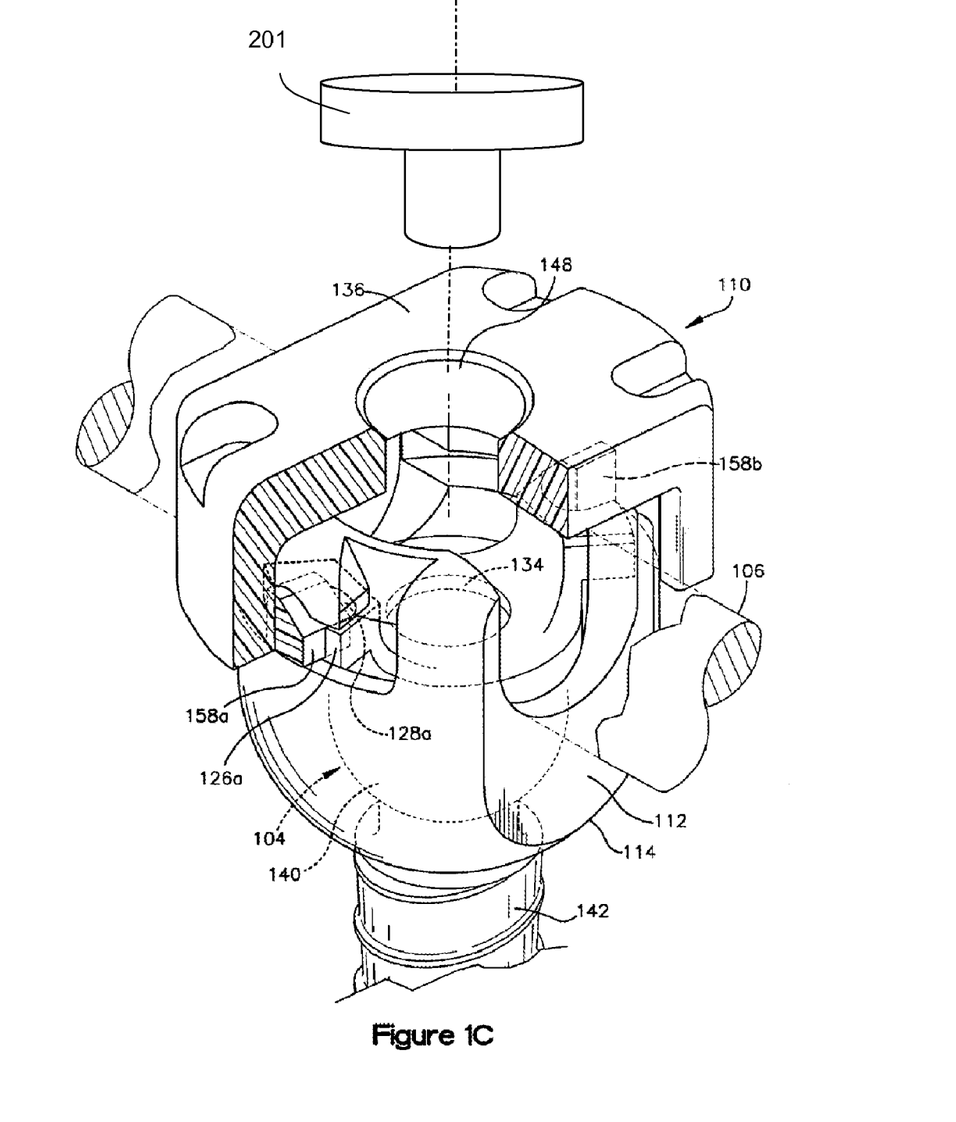
Figure 2A:
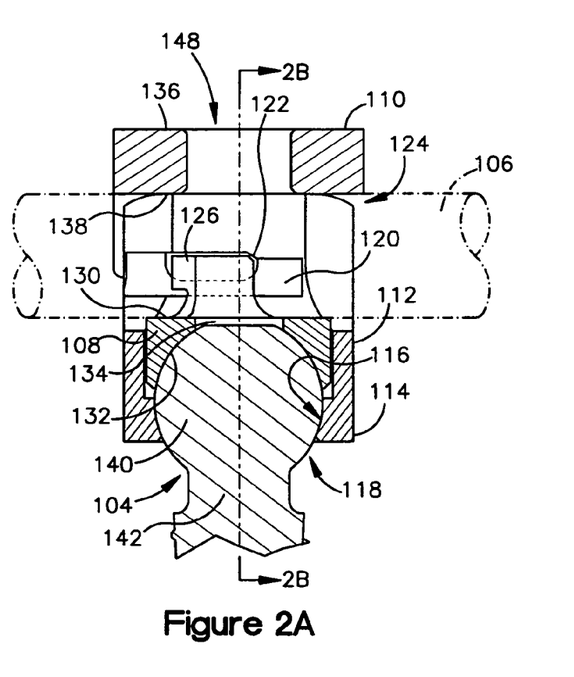
FIG. 2A is a cross-sectional side view of the locking mechanism of the present invention with a fixation device and a stabilization device showing the washer not fully engaged with the seat.
Figure 2B:
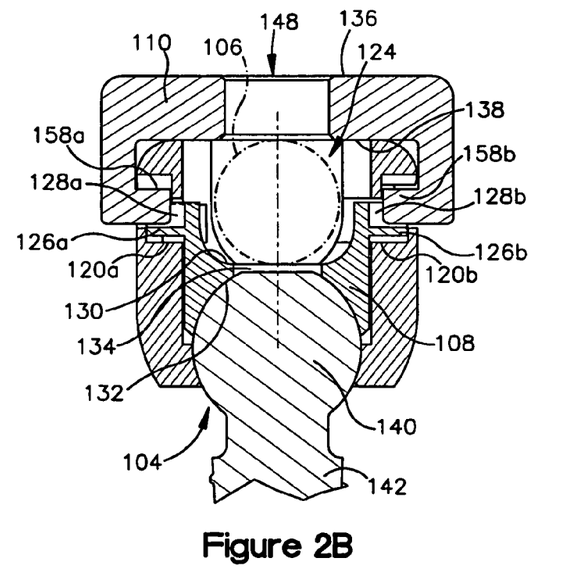
FIG. 2B is a cross-sectional front view of the locking mechanism of the present invention with a fixation device and a stabilization device showing the washer not fully engaged with the seat.
Figure 2C:
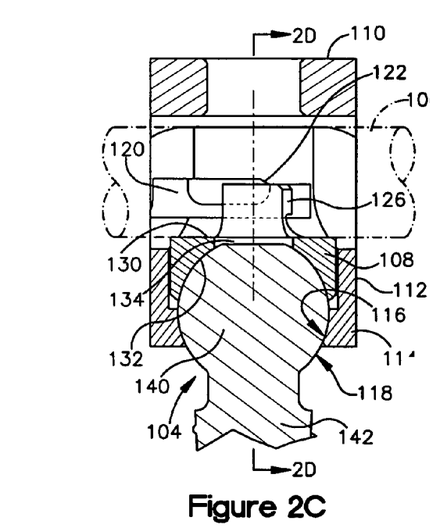
FIG. 2C is a cross-sectional side view of the locking mechanism of the present invention with a fixation device and a stabilization device showing the washer fully engaged with the seat.
Figure 2D:
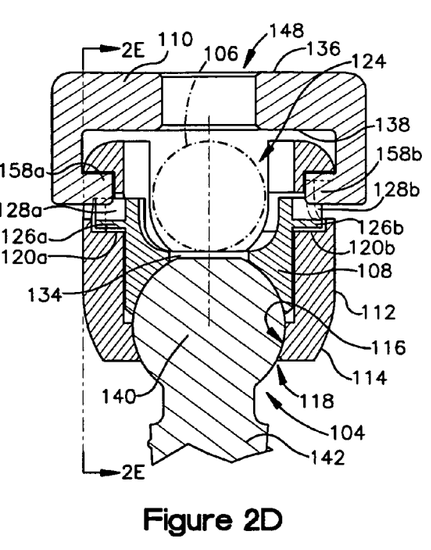
FIG. 2D is a cross-sectional front view of the locking mechanism of the present invention with a fixation device and a stabilization device showing the washer fully engaged with the seat.

Turning now to FIGS. 2A-D, the locking mechanism 100 of the present invention is illustrated in greater detail. FIGS. 2A and 2C are cross-sectional side views of the locking mechanism 100 of the present invention with a stabilization device 106, as well as a fixation device 104 in unlocked and locked positions, respectively. FIGS. 2B and 2D are cross-sectional front views of the locking mechanism 100 of the present invention with a stabilization device 106, as well as a fixation device 104 in unlocked and locked positions, respectively.

The locking mechanism 100 includes a seat 102, a washer 108 and a cap 110 for locking a fixation device 104. The locking mechanism 100 may also include a locking element for engaging a stabilization device 106. Each of the seat 102, fixation device 104, stabilization device 106, washer 108, cap 110 and locking element may be made from a variety of materials known in the art and preferably are made from biocompatible materials when the locking mechanism 100 is used for bone fixation. Such materials include, but are not limited to, titanium, titanium alloys (e.g. titanium/aluminum/vanadium (Ti/Al/V) alloys), cobalt-chromium alloys, stainless steel, ceramics (alumina ceramic, zirconia ceramic, yttria zirconia ceramic, etc.), high strength polymers (e.g. PEEK, PEKK, etc.), pyrolytic carbon, tantalum, carbon composite materials and combinations thereof. Some materials are more appropriate for fixation surfaces, such as cobalt-chromium alloys, titanium, and (Ti/Al/V) alloys, but any material known in the art for use with fixation surfaces can be used in the present invention. Such materials are commonly used in bone fixation and the like. Preferably, the materials are rigid and in one embodiment, the seat 102, fixation device 104, stabilization device 106, washer 108 and cap 110 are all made from Ti/Al/V alloys, such as Ti/6Al/4V ELI.

While one of skill in the art will recognize that fixation devices 104 other than a screw can be used without departing from the scope of the present invention, a screw is shown and described herein to illustrate the engagement of the fixation device 104 and the seat 102, as well as the method for locking the relative positions of a fixation device 104 and a stabilization device 106. Furthermore, various types of screws may be used. Two exemplary types of screws are illustrated in FIGS. 5A and 5B.

The size of the seat 102 may be similar to that of prior art devices. For example, the height of seat 102 may range from about 0.25 inch to about 1 inch. In one embodiment, the height of the seat 102 ranges from about 0.4 inch to about 0.45 inch. Also, the width of seat 102 may range from about 0.25 inch to about 1 inch. In one embodiment, the width of the seat 102 ranges from about 0.39 inch to about 0.42 inch.

The seat 102 has a side portion 112 and a bottom portion 114. The bottom portion 114 may be tapered as shown in FIGS. 2B and 2D and includes a socket 116 and a hole 118. When the locking mechanism 100 is used for spinal fixation, "above" means posterior with respect to the patient and "below" means anterior with respect to the patient. Thus, the bottom portion 114 of the seat 102 is anterior with respect to the patient and the fixation device 104 and stabilization device 106 are received by the seat 102 as the fixation device 104 and stabilization device 106 are moved in a posterior to anterior direction. Also, because the general shape of the type of seat 102 illustrated in FIGS. 1A-C and 2A-D somewhat resembles a tulip flower, this type of seat 102 is often referred to as a "tulip" by those skilled in the art.

The socket 116 is preferably sized to accept a fixation device 104, such as a screw, and the hole 118 is preferably sized to prevent the fixation device 104 from passing entirely therethrough. The hole 118 is preferably located at the bottom of the seat 102. The socket 116 is configured for engagement of the fixation device 104, or more specifically, the engagement surface 146 of the head 140 of the fixation device 104. In order to facilitate engagement, the surface of the socket 116 may include a rough or knurled surface and/or a surface fixation mechanism, such as ridges, grooves, bumps, pips, or the like. In addition, an engagement surface 146 of the head 140 of the fixation device 104 may have a similar surface.

The side portion 112 includes grooves 120 for engaging the washer 108. After placement of the fixation device 104 through the hole 118 of the bottom portion 114 of the seat 102, the washer 108 may be placed into the seat 102 from an opening in the top of the seat 102. Preferably, the washer 108 has wings 126 that extend laterally from the body of the washer 108. The grooves 120 may be parallel-sided within the seat 102, but may also be angled to help prevent splay when engaging the wings 126 of the washer 108. When placed in the seat 102, the washer 108 is preferably oriented so that the wings 126 reside within the channel 124 of the seat 102. Once within the seat 102, the washer 108 can be rotated to engage the grooves 120 of the side portion 112 of the seat 102 to prevent the washer 108 from retracting from the seat 102.

As shown, the wings 126 of the washer 108 are engageable with the grooves 120. Preferably, the grooves 120 are configured for more than one level of engagement with the wings 126. As illustrated, each of the grooves 120 narrows to create a tighter engagement as the washer 108 is rotated. For example, the grooves 120 may include an angle of activation 122 that narrows the channel and causes tighter engagement of the grooves 120 and the wings 126. Preferably, the angle of activation narrows the top part of the groove 120, which forces the washer 108 down onto the fixation device 104 to cause at least a partial locking of the position of the fixation device 104. It will be appreciated by those skilled in the art that other mechanisms for preventing the wings 126 from disengaging can be used, such as threaded grooves 120 and wings 126. In addition, the washer 108 may be configured such that a stabilization device 106 can be placed between the wings 126 without first engaging the wings 126 and the grooves 120. In this configuration, the washer 108 is preferably capable of being rotated a sufficient amount without the wings 126 butting against the stabilization device 106.

It will be understood by those of skill in the art that other types of engagement can be used. For example, rather than using a groove 120 that narrows, the outer edge of the wings 126 may be eccentrically round such that the eccentricity causes wedging as the wings 126 are rotated. Similarly, the groove 120 can be eccentric such that eccentricity of the groove 120 causes wedging.

It will be understood by those skilled in the art that the washer 108 may be engageable with the seat 102 such that the washer 108 does not pass through the side portion 112 of the seat 102. For example, the washer 108 may be configured for locking engagement with grooves, such as grooves 120, of the side portion 112 of the seat 102. The washer 108 and seat 102 may also be configured for engagement using any other suitable locking mechanism known in the art. The washer 108 may be engageable with the seat 102 such that the interaction of the washer 108 and the seat 102 alone is sufficient to lock the position of the fixation device 104.

It will be understood by those skilled in the art that a tool can be used to cause the washer 108 to engageable with the side portion 112. For example, if the washer 108 is rotatably engageable with the side portion 112, the tool may be attach to the washer 108 and be used to place the washer 108 at the appropriate position for engagement, and then be used to rotate the washer 108 to cause engagement with the side portion 112.

The seat 102 also has a channel 124 in the side portion 112 for receiving the stabilization device 106, such as a rod. While a channel 124 is preferred for receiving the stabilization device 106, it will be understood by those skilled in the art that an aperture in the side portion 112 could also receive the stabilization device 106, though a seat 102 with an aperture may be more cumbersome to use during surgery as a surgeon would have to thread the stabilization device 106 through the aperture instead of placing the stabilization device in the channel 124. Using a channel 124 to receive the stabilization device 106 provides greater flexibility for a surgeon.

After placement of the stabilization device 106 within the channel 124, it is desirable to retain the stabilization device 106 within the seat 102 and fix the position of the fixation device 106. A cap 110 retains the stabilization device within the seat 102 and interacts with the washer 108 and seat 102 to fix the fixation device 104.

Figure 2E:
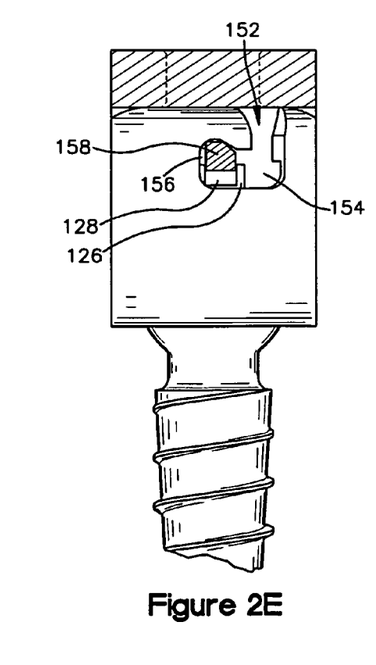
FIG. 2E is a side view of the washer, cap and locking channel of the side portion of the seat with the cap not fully engaged.

FIG. 2E illustrates the engagement of the side portion 112 of the seat 102, the washer 108 and the cap 110. The side portion 112 includes locking channels 152 configured for engagement with both the washer 108 and the cap 110. The locking channels 152 may be, for example, non-threaded, non-wedging channels. Preferably, the locking channels 152 extend to the grooves 120 and are J-shaped channels. Once the wings 126 are engaged with grooves 120, a portion of each of the wings 126 is exposed to the locking channel 152. The exposed portion of each wing 126 preferably comprises a female receiver 128 for mating engagement with the cap 110.

Preferably, the washer 108 is rotated such that the female receivers 128 are aligned with alignment portions 154 of the locking channels 152. Once the female receivers 128 are properly aligned, the cap 110 is placed over the seat 102 such that male members 158 of the cap 110 engage the locking channels 152 and the female receivers 128. After engagement, the cap 110 and washer 108 combination is then rotated such that the male member 158 and female receiver 128 combination enters the locking portion 156 of the locking channel 152. The locking portion 156 is preferably a pull-up lock that prevents the combination from backing out. Accordingly, when the cap 110 is pulled up, the male member 158 is restrained from unlocking by the tip of the "J" shape of the locking channel 152.

In addition, the male members 158 may be configured such that the male members 158 partially tear off when the cap 110 is disengaged after being fully engaged in the locking channel 152. This may occur, for example, during revision surgery. The cap 110 may then be discarded and a new cap 110 having slightly different shaped male members 158 may be used to create a new locking engagement.

The rotation of the cap 110 to a locked position causes the washer 108 to further engage the grooves 120, thereby locking the fixation device 104 with respect to the seat 102. The stabilization device 106, however, is not locked by the rotation of the cap 110 and washer 108. Rather, the stabilization device 106 can be repositioned as necessary during a procedure involving the use of the locking mechanism 100. Accordingly, the fixation device 104 is locked independent of the stabilization device 106.

It will be understood by those of skill in the art that the fixation device 104 may be locked and unlocked multiple times prior to locking the stabilization device 106. This is particularly advantageous for surgical procedures involving multiple locking mechanisms 100 and stabilization devices 106 because the locking mechanism 100 is capable of maintaining the position of a polyaxial fixation device 104 while the remainder of the surgical implants are fitted and installed. This also facilitates less invasive surgical procedures as the seats 102 and fixation mechanisms 104 maintain their position more effectively prior to locking the entire system in fixed position.

Figure 3A:
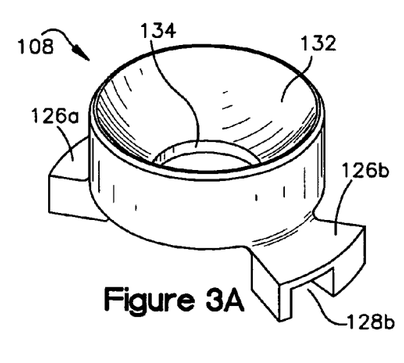
FIGS. 3A-B are top perspective and bottom perspective views of a washer according to the present invention.
Figure 3B:
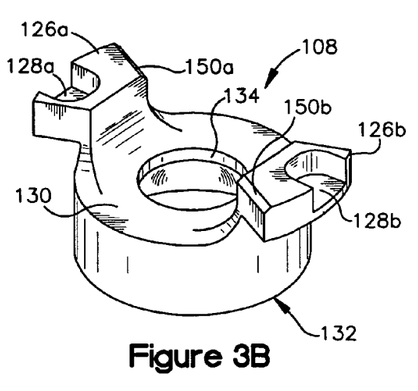

Turning now to FIGS. 3A and 3B an exemplary washer 108 for use with the seat 102 of FIGS. 1A-1C and 2A-2E is illustrated. The washer 108 is configured for placement between a fixation device 104 and a stabilization device 106 and functions to lock the fixation device 104 in a fixed position. The washer 108 may be made from a titanium alloy and has a fixation device side 132 and a stabilization device side 130. The surfaces of the fixation device side 132 and/or the stabilization device side 130 may be relatively smooth, or may have a rough or knurled surface and/or a surface fixation mechanism, such as ridges, grooves, bumps, pips, or the like to increase the surface coefficient of friction. For example, the stabilization device side 130 or fixation device side 132 may be roughened by aluminum oxide blasting.

One of skill in the art will understand that other surface treatments may also be used on the surfaces of the fixation device side 132 and stabilization device side 130. One of skill in the art will also understand that any of the surfaces of the locking mechanism 100, any of the surfaces of the fixation device 104 and/or any of the surfaces of the stabilization device 106 may also be surface treated.

The fixation device side 132 may also be contoured to improve engagement with the fixation device 104. The contour may increase the area over which the washer 108 and fixation device 104 are engaged. For example, if the locking mechanism 100 is being used to engage a fixation screw 104 with a generally spherical head 140, the head fixation side 132 may be contoured such that it includes a channel with a curvature that approximates the curvature of the head 140. Similarly, the stabilization device side 130 may be contoured to increase the area over which the washer 108 and stabilization device 106 are engaged. Where the stabilization device 106 is a rod, the stabilization device side 130 may be contoured such that it includes a channel with a curvature that approximates the curvature of the outer surface of the rod. It will understood by those in the art that the contour may alternatively decrease in the area over which the washer 108 and fixation device 104 are engaged.

Also, the fixation device side 132 may be designed so that it enhances the fixation of the fixation device 104 to a target. For example, the fixation device side 132 may include interdigitating fingers, ridges or other mechanism for increasing the interaction between the fixation device side 132 and the fixation device 104, such as a screw.

In the exemplary embodiment of FIGS. 1A-C, 2A-D and 3A-B, the washer 108 is rotatably engageable with grooves 120a and 120b of the side portion 112 of the seat 102. Accordingly, the washer 108 includes wings 126a and 126b for engagement with grooves 120a and 120b. Each of the wings 126a and 126b preferably includes a chamfer 150a and 150b, respectively, for facilitating engagement with the grooves 120a and 120b. Each of the wings 126a and 126b also preferably includes a female receiver 128a and 128b, respectively, configured for mating engagement with male member of the cap 110. When engaged, the female receivers 128a and 128b are preferably aligned with alignment portions 154a and 154b of the locking channels 152a and 152b of the side portion 112 of the seat 102.

In addition, the washer 108 may include an access hole 134 for providing access to the fixation device 104 after the washer 108 is at least partially engaged with the side portion 112 of the seat 102. Thus, when the washer 108 is either not engaged, partially engaged or fully engaged with the side portion 112, a drive mechanism can pass through the access hole 134 to exert drive force on the fixation device 104.

Those skilled in the art will understand that the specific shapes and types of the grooves 120a and 120b and wings 126a and 126b may vary substantially. For example, the grooves 120 may include miniature slots on their interiors to interact with small bumps on the wings 126 so that it is apparent when the wing 126 and groove 120 are properly engaged. Similarly, the wings 126 may each have a surface with small ridges to create increased friction between the wings 126 and the grooves 120 to help prevent the washer 108 from disengaging. Such surfaces may be rough or knurled and/or include at least one surface fixation mechanism, such as ridges, grooves, bumps, pips, or the like to increase the surface coefficient of friction. For example, the surfaces may be roughened by aluminum oxide blasting. One of skill in the art will understand that other surface treatments may also be used.

It will also be understood by those skilled in the art that an intermediate element may be used between the washer 108 and either or both the fixation device 104 and stabilization device 106 without departing from the scope of the present invention. For example, the intermediate element may be a spacer between the washer 108 and the fixation device 104. The spacer may thus be configured to have contoured surface, and/or interdigitating fingers, like those described with reference to the fixation device surface 132 of the washer 108.

Similarly, in intermediate element between the washer 108 and stabilization device 106 may have a surface similar to the stabilization device surface 130.

Figure 4A:
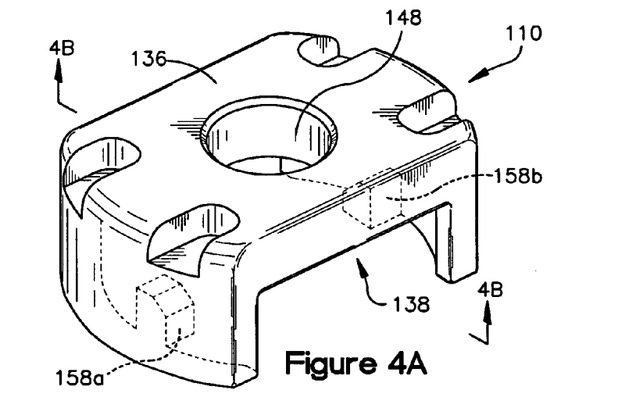
FIGS. 4A-B are top perspective and bottom perspective views of a cap according to the present invention.
Figure 4B:
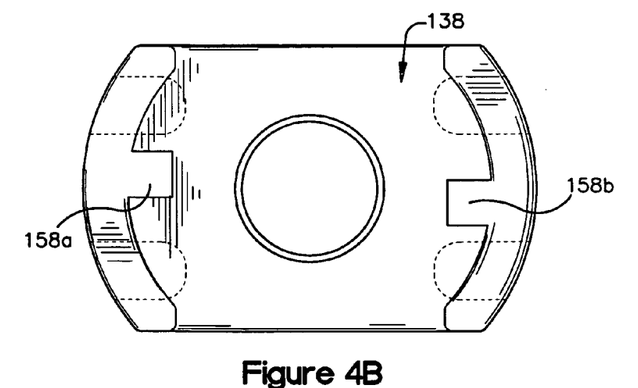

FIGS. 4A and 4B illustrate an exemplary cap 110 for use with the seat 102 of FIGS. 1A-C and 2A-F. As described above, the cap 110 retains the stabilization device 106 in the channel 124 and engages the washer 108 to cause fixation of the fixation device 104. In addition to the cap 110 illustrated, the cap 110 may be, for example, hingedly connected to the seat 102, either vertically or horizontally.

In the specific embodiment of FIGS. 1A-1C, 2A-2E and 4A-4B, the cap 110 is longer in one direction than in the other. The cap 110 is preferably placed on the seat 102 such that it is generally perpendicular to the major axis of the stabilization device 106. The cap 110 preferably has a top surface 136 and a stabilization device surface 138. The stabilization device surface 138 may include a contour that approximates the outer surface of the stabilization device 106. In addition, the cap 110 may also have an access hole 148 for facilitating locking engagement of the stabilization device 106 within the seat 102. The locking of the stabilization device 106 may be accomplished by a locking element (not shown) passing through the access hole 148.

The cap 110 also preferably has male members 158a and 158b for engaging locking channels 152a and 152b and female receivers 128a and 128b. When placed on the seat 102, the male members 158a and 158b preferably engage the locking channels 152a and 152b and the female receivers 128a and 128b. The male members 152 and female receivers 128 may be disengageably engageable in the alignment portion 154 of the locking channel 152. The cap 110 can then be rotated, thereby causing the washer 108 to rotate. The male members 158a and 158b are positioned in the locking portions 156a and 156b of the locking channels 152a and 152b where the male members 152 and female receivers 128 may be lockingly engageable. Locking is accomplished as described above with reference to FIG. 2E.

It will be understood by those of skill in the art that engagement of the cap 110 and washer 108 may also be accomplished without using male members 158 and female receivers 128. For example, the surfaces of the cap 110 and washer 108 may be configured to have grooves, ridges, a fork around the wings of the washer 108, or the like to cause engagement of the cap 110 and washer 108.

It will be understood by those skilled in the art that the locking mechanism may also include a locking element (not shown) for fixing the position of the stabilization device 106. The locking element may be configured to interact with the cap 110 to cause engagement of the stabilization device. For example, the locking element may be a screw, such as a breakaway screw, that passes through the access hole 148, which may be threaded. The locking element may act to force the cap 110 away from the stabilization device 106 and force the male members 158 into the tip of the locking portion 154 of the locking channels 152, thereby locking the cap 110. As this happens, the locking element may force the stabilization device 106 down into the washer 108, thereby locking the stabilization device 106 into position. Other mechanisms for locking the stabilization device 106 may also be used, so long as the stabilization device 106 is locked independent of the fixation device 104. Examples of such locking elements include, for example: a screw, a breakaway screw, a 90 degree wedge, a linear wedge, a washer and nut, a snap-in lock, or the like.

In use, the fixation mechanism 100 of the present invention provides a convenient method for engaging and locking a relative position of a fixation device 104 and a stabilization device 106. According to one aspect of the present invention, the fixation device 104 is passed through the bottom portion 114 of the seat 102 and then fixed to a target, such as a spinal vertebra or other bone. A washer 108 is then engaged with a side portion 112 of the seat 102 such that a receiver 128 on the washer 108 and locking channel 152 on the side portion 112 of the seat are aligned. A stabilization device 106 is placed in a side portion 112 of the seat 102. In a specific embodiment, the stabilization device 106 is placed in a channel 124. Following placement of the stabilization device 106, a cap 110 having a male member 158 is placed atop the seat 102 such that the male member 158 engages the locking channel 152 and the receiver 128. The fixation device 104 is then locked with respect to the seat 102. Locking of the fixation device 104 may be accomplished by rotating the combination receiver 128 and male member 158 from an alignment portion 154 of the locking channel 152 into a locking portion 156 of the locking channel 152.

In addition, the stabilization device 106 may be locked with respect to the seat 102 after the fixation device 104 is at least temporarily locked. To lock the stabilization device 106, a locking element may be engaged. Also, it will be understood by those skilled in the art that part of the seat 102 may be peened such that the fixation device 104, washer 108 and seat 102 essentially function as a single piece. This minimizes the number of steps required during installation of the locking mechanism 100.

While the present invention has been described in association with exemplary embodiments, the described embodiments are to be considered in all respects as illustrative and not restrictive. Such other features, aspects, variations, modifications, and substitution of equivalents may be made without departing from the spirit and scope of this invention which is intended to be limited only by the scope of the following claims. Also, it will be appreciated that features and parts illustrated in one embodiment may be used, or may be applicable, in the same or in a similar way in other embodiments.

What is claimed is:

1. A locking mechanism for engaging and locking a relative position of a bone fixation device and a relative position of a stabilization device, the locking mechanism comprising: a seat comprising a bottom portion structured and dimensioned to receive the fixation device and prevent the fixation device from passing entirely therethrough and a side portion extending along a first direction from said bottom portion and comprising a channel for receiving the stabilization device; a washer with wings structured and dimensioned to engage grooves within the side portion of the seat between the stabilization device and the fixation device, wherein at least one of said wings comprises a receiver structured to pass partially through and align with a locking channel in the side portion of the seat along a second direction being perpendicular to said first direction; and a cap structured and dimensioned to engage directly with the receiver through the locking channel of the seat along said second direction to lock the bone fixation device with respect to the bottom portion of the seat independent of the stabilization device; and a locking element structured and dimensioned for locking the stabilization device with respect to the seat by compressing the stabilization device to the washer.

2. A method for locking the relative positions of a bone fixation device and a stabilization device comprising: placing a bone fixation device along a first direction through a bottom portion of a seat of a locking mechanism; engaging a washer having a receiver with a side portion of the seat along a second direction being perpendicular to said first direction wherein said side portion comprises a locking channel such that the receiver of the washer passes partially through and is aligned with the locking channel of the seat; placing a stabilization device in a channel in the side portion of the seat; placing a cap with a male member atop the seat such that the male member engages directly with the receiver through the locking channel along said second direction; and locking the fixation device with respect to the seat.

3. A locking mechanism comprising:
a seat comprising a bottom portion and a side portion extending along a first direction from said bottom portion and wherein said bottom portion is structured and dimensioned to receive a bone fixation device;
a washer structured and dimensioned to be placed within said seat and to pass partially through and engage said side portion of the seat along a second direction being perpendicular to said first direction; and
a cap structured and dimensioned to engage directly with the washer through the side portion of the seat along said second direction to lock the bone fixation device.

4. The locking mechanism of claim 3 wherein the side portion of the seat comprises a channel for receiving a stabilization device.

5. The locking mechanism of claim 4 wherein the bone fixation device is locked independent of the stabilization device.

6. The locking mechanism of claim 4 wherein the channel is shaped and dimensioned to receive a rod-shaped stabilization device.

7. The locking mechanism of claim 4 wherein the washer is placed and engages the side portion of the seat between the bone fixation device and the stabilization device.

8. The locking mechanism of claim 4 wherein the washer engages and disengages the side portion of the seat after the stabilization device is placed in the channel.

9. The locking mechanism of claim 4 further comprising a locking element to lock the position of the stabilization device.

10. The locking mechanism of claim 9 wherein the locking element comprises at least one of: a screw, a breakaway screw, a washer, a 90 degree wedge, a linear wedge, a washer and nut, or a snap-in lock.

11. The locking mechanism of claim 9 wherein the locking element locks the position of the stabilization device by compressing the stabilization device onto the washer.

12. The locking mechanism of claim 4 wherein the washer comprises a stabilization device side that is contoured to interact with a contour of the stabilization device.

13. The locking mechanism of claim 4 wherein the cap comprises a stabilization device side that is contoured to interact with a contour of the stabilization device.

14. The locking mechanism of claim 3 wherein the washer permits access to the bone fixation device after the washer is at least partially engaged with the side portion of the seat.

15. The locking mechanism of claim 3 wherein the washer comprises at least one wing and the side portion of the seat comprises at least one groove to receive the at least one wing of the washer.

16. The locking mechanism of claim 15 wherein the at least one groove of the side portion of the seat is a wedging groove.

17. The locking mechanism of claim 3 wherein the washer comprises at least one female receiver and the cap comprises at least one male member and wherein the at least one female receiver and the at least one male member are structured and dimensioned for mating engagement through the side portion of the seat.

18. The locking mechanism of claim 3 wherein the cap comprises at least one male member and the side portion of the seat comprises at least one locking channel structured and dimensioned to receive the at least one male member of the cap.

19. The locking mechanism of claim 18 wherein the washer comprises at least one female receiver alignable with the at least one locking channel and the at least one male member.

20. The locking mechanism of claim 19 wherein the at least one locking channel comprises an alignment portion and a locking portion and wherein the at least one female receiver and the at least one male member are disengagably engageable in the alignment portion and lockingly engageable in the locking portion.

21. The locking mechanism of claim 19 wherein the at least one locking channel is a J-shaped channel.

22. The locking mechanism of claim 3 wherein the washer comprises a bone fixation device side that is contoured to interact with a contour of the bone fixation device.

23. The locking mechanism of claim 3 wherein the bottom portion is structured and dimensioned to prevent the bone fixation device from passing entirely therethrough.

24. The locking mechanism of claim 3 wherein the bottom portion of the seat comprises a socket tapered to receive and engage the bone fixation device.

25. The locking mechanism of claim 3 wherein the bottom portion of the seat is structured to receive a screw-type bone fixation device and wherein said screw-type bone fixation device comprises a shaft and a head and the bottom portion of the seat comprises a hole that is larger than the shaft and smaller than the head.

26. The locking mechanism of claim 3 wherein the washer and the side portion of the seat are rotatably engageable to lock the bone fixation device.

27. A locking mechanism comprising:
a seat comprising a bottom portion and a side portion extending along a first direction from said bottom portion and wherein said bottom portion is structured and dimensioned to receive a bone fixation device;
a washer structured and dimensioned to be placed within said seat and to pass partially through and engage said side portion of the seat along a second direction being perpendicular to said first direction;
a cap structured and dimensioned to engage directly with the washer through the side portion of the seat along said second direction to lock the bone fixation device; and
wherein the washer comprises at least one female receiver and the cap comprises at least one male member and wherein the at least one female receiver and the at least one male member are structured and dimensioned for mating engagement through a locking channel in the side portion of the seat.

28. A locking mechanism comprising:
a seat comprising a bottom portion and a side portion extending along a first direction from said bottom portion wherein said bottom portion is structured and dimensioned to receive a bone fixation device;
a washer structured and dimensioned to be placed within said seat and to pass partially through and engage said side portion of the seat along a second direction being perpendicular to said first direction;
and a cap structured and dimensioned to engage directly with the washer through the side portion of the seat along said second direction to lock the bone fixation device; and wherein the cap comprises at least one male member and the side portion of the seat comprises at least one locking channel structured and dimensioned to receive the at least one male member of the cap.

29. A locking mechanism comprising:
a seat comprising a bottom portion and a side portion extending along a first direction from said bottom portion wherein said bottom portion is structured and dimensioned to receive a bone fixation device;
a washer structured and dimensioned to be placed within said seat and to pass partially through and engage said side portion of the seat along a second direction being perpendicular to said first direction;
a cap structured and dimensioned to engage directly with the washer through the side portion of the seat along said second direction to lock the bone fixation device; and
a locking element to lock the position of a stabilization device placed in a channel of said side portion.

30. A locking mechanism comprising:
a seat comprising a bottom portion and a side portion extending along a first direction from said bottom portion wherein said bottom portion is structured and dimensioned to receive a bone fixation device;
a washer structured and dimensioned to be placed within said seat and to pass partially through and engage said side portion of the seat along a second direction being perpendicular to said first direction;
a cap structured and dimensioned to engage directly with the washer through the side portion of the seat along said second direction to lock the bone fixation device; and
wherein the washer is further structured and dimensioned to permit access to the fixation device after the washer is at least partially engaged with the side portion of the seat.

* * * * *